United States Patent

Leveen et al.

[11] Patent Number: 4,988,355
[45] Date of Patent: Jan. 29, 1991

[54] ARTERIAL CLAMP

[76] Inventors: Eric G. Leveen, 19 Palmetto Rd., Charleston, S.C. 29407; Robert F. Leveen, 312 Lombard St., Philadelphia, Pa. 19147

[21] Appl. No.: 464,546

[22] Filed: Jan. 16, 1990

[51] Int. Cl.⁵ .............................................. A61B 17/00
[52] U.S. Cl. ..................................... 606/158; 606/151
[58] Field of Search ....................... 606/151, 157, 158; 128/325; 24/16 PB, 17 AP, 30.5 P

[56] References Cited

U.S. PATENT DOCUMENTS

| 3,993,076 | 11/1976 | Fogarty | 606/158 |
| 4,346,869 | 8/1982 | MacNeil | 606/157 |
| 4,390,019 | 6/1983 | LeVeen et al. | 606/158 |
| 4,800,876 | 1/1989 | Golyahovsky et al. | 606/158 |
| 4,835,824 | 6/1989 | Durham et al. | 606/157 |

FOREIGN PATENT DOCUMENTS

| 0184542 | 6/1986 | European Pat. Off. | 606/157 |
| 2177748 | 1/1987 | United Kingdom | 606/157 |

Primary Examiner—Randall L. Green
Assistant Examiner—Gary Jackson
Attorney, Agent, or Firm—Gipple & Hale

[57] ABSTRACT

A surgical clamp comprising a pair of arms, each arm being interconnected at one end to one end of the other arm by a flexible, resilient member normally urging said arms apart while maintaining facing surfaces. A clamping strip of resilient material is mounted on the arms, the resilient material being softer than the material of the clamping arms. A releasable ratchet assembly including a ratchet body and flexible tubing is positioned on the opposite end of one of the arms extending toward and being engageable with a holding lip on the other arm, so that when the arms are moved toward each other, the arms can be held in fixed relative positions, mounted to said body.

10 Claims, 2 Drawing Sheets

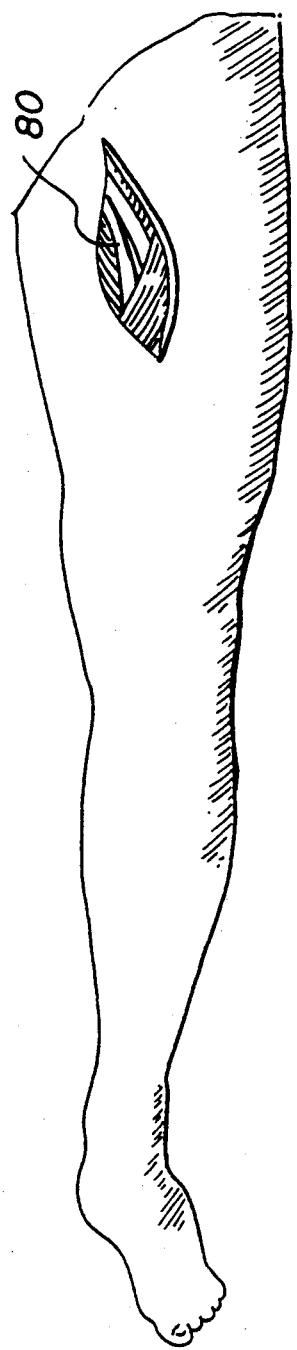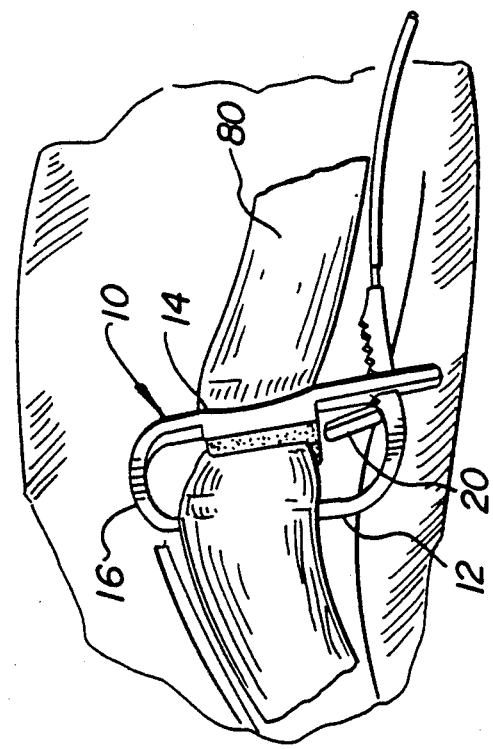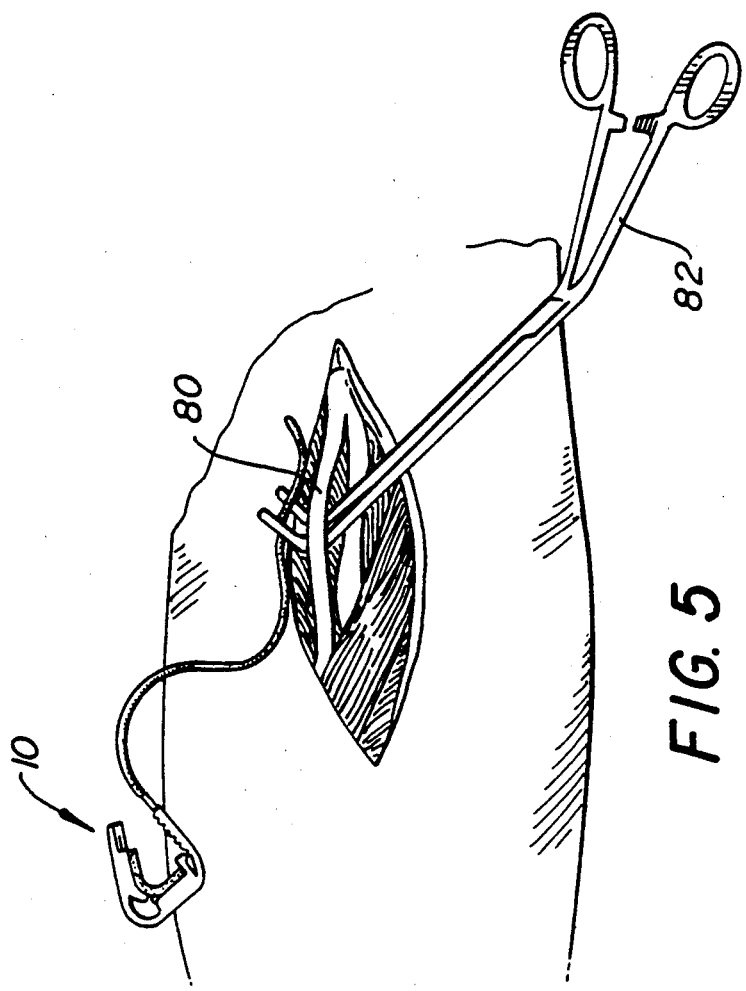

ARTERIAL CLAMP

FIELD OF THE INVENTION

This invention generally relates to clamp and, more particularly, to an arterial clamp for stopping the flow of blood from a blood vessel.

DESCRIPTION OF THE PRIOR ART

In the course of vascular surgery, it is often necessary to temporarily occlude a major artery in order to repair it, to clean out its contents or to anastomose it to another blood vessel.

Formerly, it was the custom to double a tubing or tape underneath the blood vessel so that when two ends of the tape were put under tension the vessel was occluded in a circumferential fashion. The vessel loops are then kept under tension by attaching them to the sterile drapes surrounding the incision. This practice is unsatisfactory since the tension exerted on the drapes pulls then from their position. This movement which displaces the drapes and relaxes the tape causes bleeding from the opened vessel.

Another means of occlusion uses an occluding clamp, and the clamp must not only gently squeeze the vessel but must also evenly compress the vessel without injury. A spring loaded clamp with fixed tension is not satisfactory, as provision must be made for adjustment of the clamping pressure. Thus, the pressure must not be more than necessary to occlude the blood vessel, and gradual release of the pressure is desirable to permit a small flow of blood to test any suturing before the clamp is fully opened. Also, after the clamp is applied, it should not have an opening through which the vessel can be accidently dislodged and cause a serious loss of blood.

Various types of clamps with soft, vessel engaging surfaces and ratchet type holding mechanisms are known in the art. See, for example, U.S. Pat. Nos. 3,174,754, 3,503,398 and 3,766,925. Some of the prior art clamps are cumbersome or awkward to use and/or expensive to make.

There are a number of prerequisites for a satisfactory, easily-used, and effective arterial clamp. Most important is that it does not cause injury to the vessel's intima. A small plastic clamp as disclosed by U.S. Pat. No. 4,390,019 has many desirable characteristics as a clamp. It does not crush the intima, its jaws close parallel, and it could be opened a ratchet at a time to allow a trickle of blood through an arterial vessel proximal to a sutured anastomosis. These are all desirable features for an arterial occlusive clamp. The ratchet feature allowed for gradual opening of the clamp which permitted testing of the suture line at low pressures and flows. Most other non-traumatic clamps totally compress the vessel until removed. Despite the acceptable features of this clamp, it had serious defects which seriously limited its usefulness. The clamp was too difficult to place around the vessel and required considerable agility and space to position the lower jaw beneath the blood vessel.

Thus the present invention was developed. This invention is a simple surgical clamp which is readily applied to a blood vessel, is easily adjustable, provides the desired clamping pressure without injury to a vessel and, after application, does not have a side opening through which the blood vessel can be displaced.

SUMMARY OF THE INVENTION

The present invention describes a new clamp which employs a hollow tubular vessel loop of an elastomeric material which is attached to the lower end of the opened jaw of the clamp. There are no obstructions and no impediments which hamper its placement. It thus becomes unnecessary to use elastomeric tape or tubing to occlude the vessel instead of using a clamp which would ordinarily require much more dissection. In the preferred embodiment of the inventive clamp at least the major portion of the clamp is made in one piece from a plastic material. The major portion comprises a pair of clamping arms or jaws which are generally parallel when the clamp is closed and are interconnected at one end by a flexible, resilient member which urges the arms into a separated relation. The opposite end of one arm is formed with a ratchet and tube, the ratchet extends toward and engages a lip portion defined by the other arm so as to hold the arms in the positions at which they are set as the clamp is applied. However, the other arm can be released from the ratchet to decrease clamping pressure or to open the clamp for insertion of a blood vessel between the clamping arms.

The clamping portions of the arms define slots for receiving and holding protrusions of a soft, resilient strip which engages the blood vessel. The clamping portion of one arm has a projection or bracket member at one end for preventing dislodgement of a blood vessel in one direction, and the clamping portion of the other arm has a similar projection or bracket member displaced from the first-mentioned projection for preventing dislodgement of a blood vessel in the opposite direction.

Other objects and advantages of the present invention will be apparent from the following detailed description of the presently preferred embodiment thereof, which description should be considered in conjunction with the accompanying drawings in which:

BRIEF DESCRIPTION OF THE DRAWINGS

FIG. 4 is a perspective view of a leg opened revealing the blood vessel to be clamped;

FIG. 5 is a perspective view of the invention shown in FIG. 1 with the tubing portion of the clamp being pulled around the blood vessel to be clamped: and FIG. 6 is a perspective view of the clamp clamping the blood vessel shown in FIG. 5.

DETAILED DESCRIPTION OF THE DRAWINGS

Figure 1:
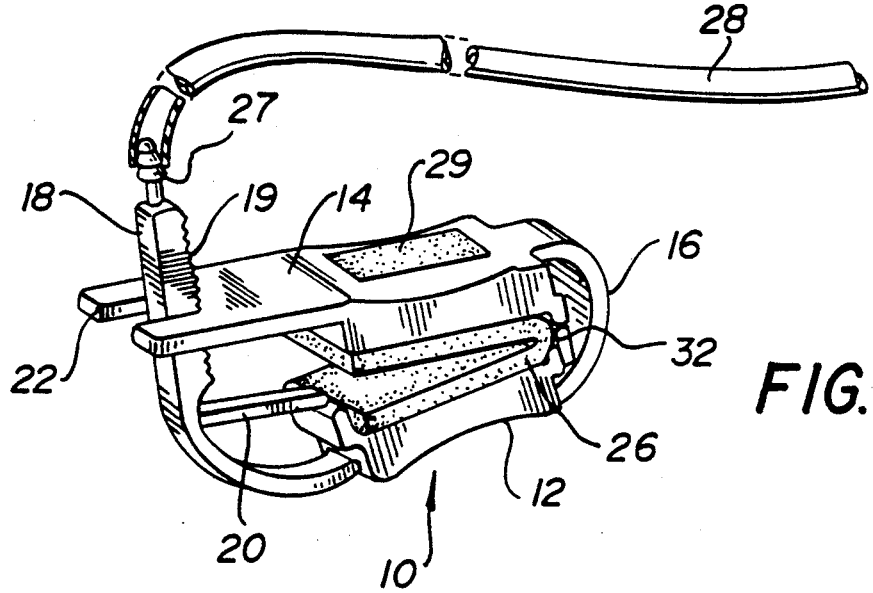
FIG. 1 is an isometric view of the preferred embodiment of the clamp of the invention.
Figure 2:
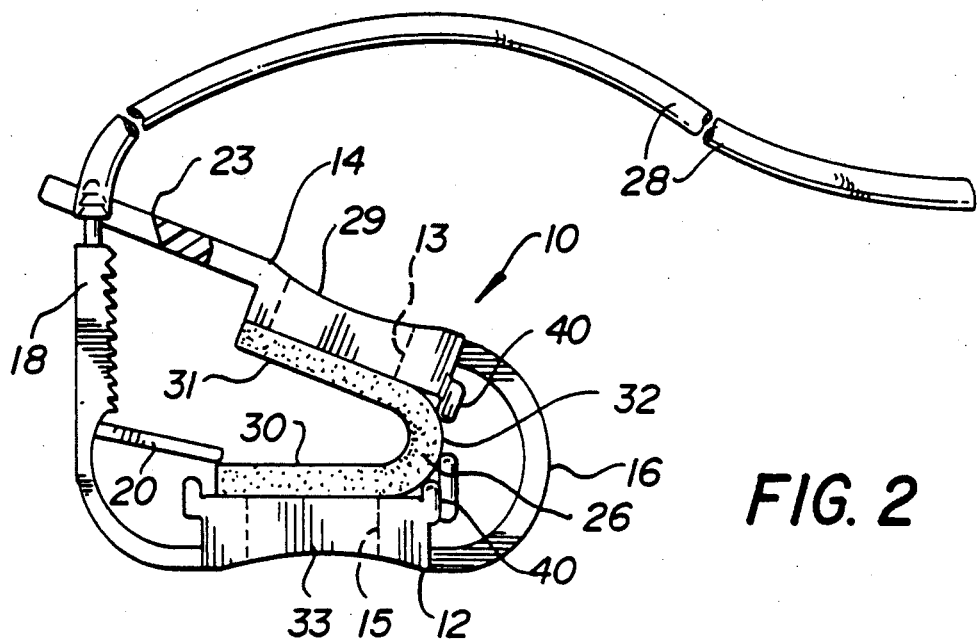
FIG. 2 is a side elevation view of the embodiment show in FIG. 1 with the clamp in its released position.

In the preferred embodiment and best mode of the invention illustrated in FIGS. 1-3 and 6, the clamp 10 has a pair of clamping arms or jaws 12 and 14 with concave finger holding portions, the arms being connected by an integral resilient member 16 which, when the ratchet 18, hereinafter described, is released, causes the arms 12 and 14 to move apart and assume the positions shown in FIG. 2. The resilient connecting member 16 also has sufficient elasticity to permit the arms 12 and 14 to be spread further apart than is shown in FIG. 2 so that a blood vessel 80 can be inserted between the arm 14 and a guide member 20 positioned below the ratchet 18 during application of the clamp 10 to the blood vessel 80. The guide member 20 extends outwardly at an angle away from ratchet 18 with its distal end almost abutting the top surface of clamping strip base portion 30 to guide the blood vessel into the clamping member 26.

Figure 3:
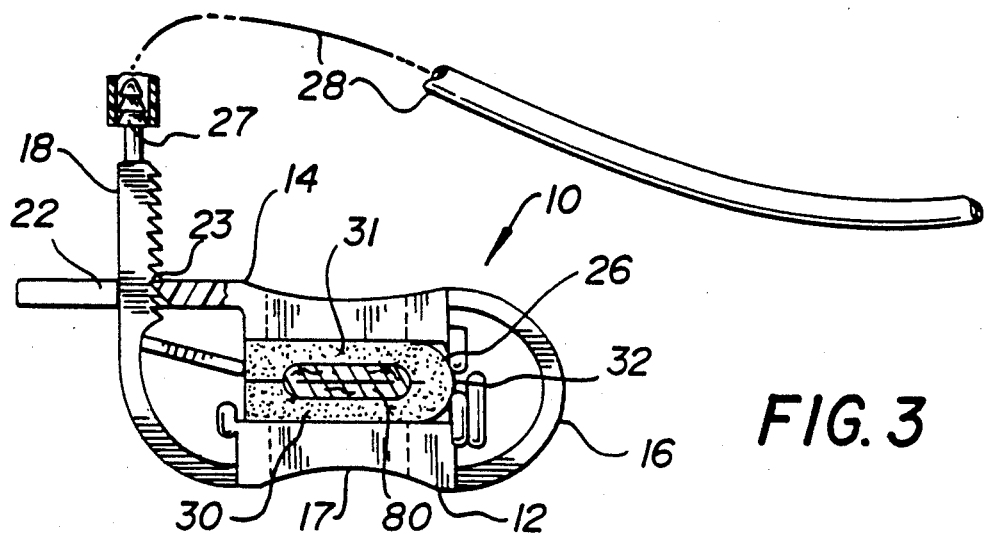
FIG. 3 is a side elevation view of the embodiment shown in FIG. 1 with the clamp receiving and clamping a blood vessel.

The connecting member 16 also has sufficient resiliency to permit the arms 12 and 14 to be brought into parallel, or substantially parallel relationship, as shown in FIG. 3.

The clamping arms 12 and 14 respectively have throughgoing slots or apertures 13 and 15 cut therein which are adapted to receive and hold projections or protrusions 29 and 33 integrally formed on the base portions 30 and 31 of the clamping strip member 26. The base portions 30 and 31 are connected together by an intermediate connecting portion 32. The base portions have respective protrusions or projections 29 and 33 extending perpendicularly therefrom which snugly fit into throughgoing slots 13 and 15 formed in arms 12 and 14 holding the clamping strip member 26 firmly in place. The base portions 30 and 31 are preferably constructed of a strip of soft, resilient material, i.e., softer than the material of the clamping arms 12 and 14. The slots 13 and 15 are tapered and the dimensions of the projections 29 and 33 are such as to fill the slots 13 and 15 as to resist dislodgement of the projections 29 and 33 from the slots 13 and 15. However, the clamping strip member 26 may be removed and replaced from the arms. Although the clamping strip 26 is a single integrally formed strip for manufacturing and blood vessel retention reasons, the clamping strip member could be constructed of two separate and identical pieces.

The ratchet member 18 provided with ratchet teeth 19 and a nipple structure 27 extends from the end of the arm 12. A tube 28 is mounted on the nipple tube holding member 27 and extends from the top of the ratchet member 18. The end of arm 14 opposite connecting member 16 extends outward and defines a slot like opening 22 therein through which the ratchet 18 can pass. The slot 22 has one open end and a blind end which forms a slip 23. The ratchet 18 is made of resilient plastic material and is formed so that it is urged toward the lip 23 at one side of the opening 22. Thus, after the ratchet 18 is inserted into the opening or slot 22, by the pressing of the arms 12 and 14 toward each other, the ratchet teeth 19 will engage the lip 23 when the arms 12 and 14 are released and will prevent separation of the arms 12 and 14 until the ratchet 18 is moved in a direction away from the lip 23. It will be observed that the width of the slot opening 22 between the lip 23 and the opposite side of the opening is greater than the corresponding dimension of the ratchet 18.

Each of the arms 12 and 14 are provided with rear brackets 40 which seat and hold the clamping portions 30 and 31 in position on the arms. Arm 12 is provided with a front bracket 42 and a second rear bracket holder 44 to keep the clamping portions and connector in place and prevent the blood vessel 80 from being dislodged between the clamping portions 30 and 31 when the clamp is applied.

Preferably, all the parts of the clamp 10, except the clamping strip 26, are injection molded in one piece from a plastics material, such as a polycarbonate, and the clamping strip 26 is separately made in one piece from soft resilient material such as a soft or sponge rubber or a cellular plastics material, such as polyurethane.

In use, a blood vessel, e.g., the blood vessel 80 (FIG. 6) easily follows the pathway of the tube 28 which is pulled beneath the blood vessel to be clamped. The upper jaw or arm 14 of the clamp, which lies superficial to the vessel, is then closed to occlude the vessel. The attachment of the hollow tubing 28 to the lower jaw or arm 12 is via a nipple-like structure 27 on the distal end of the ratchet 18. The elastomeric tubing 28 can be pulled beneath the vessel with minimal dissection using a simple right-angle clamp 82 as shown in FIG. 5. Very little room is required to pass the tube 28 beneath the vessel. Since the opened end of arm 12 of the vessel clamp is attached to the tube 28, it is easy to pull the lower jaw or arm 12 of the clamp 10 beneath the blood vessel 80. This clamp can be rapidly and easily placed with minimal dissection and is inserted with the facing surfaces 30 and 31 of the strip 26 open, as shown in FIG. 2, or with the facing surfaces of the strip 26 otherwise far enough apart to receive the blood vessel 80. The arms 12 and 14 are then pressed toward each other, with the ratchet 18 received in the opening 22, until the flow of blood from the blood vessel 80 is stopped and when the desired pressure, a matter of "feel" and visual observation, is applied to the vessel 80. The teeth 19 are then engaged with lip 23 and one of the teeth locks on lip 23 holding the clamp in a fixed position against the force exerted by connector member 16. The pressure may be reduced, if either the initial pressure is too high or if it is desired to have a small flow of blood to test suturing, by releasing the ratchet teeth 19 from the lip 23 as previously described and by maintaining gradually reduced, finger pressure on the arms 12 and 14.

The clamp 10 may be completely released by disengaging the ratchet teeth 19 from the lip 23 and permitting the arms 12 and 14 to spring apart through the force exerted by connector 26 or by deliberately spreading the arms 12 and 14 apart manually.

Thus, the clamp of the invention is simple in construction and may be made relatively easily and inexpensively.

The general configuration of the clamp and its manner of use are illustrated in the Figures. The space underneath the blood vessel for passing the clamp tubing can be dissected with a right-angle or a tonsil clamp. The tubing is then pulled through, and the clamp closed. The upper end of the ratchet jaw fits into slot 22 which allows the edge of the upper jaw 14 to engage the ratchet without the removal of the tubing. After placement, the clamp tubing can be cut off of the clamp if so desired.

A blood vessel may be readily inserted in the clamp and is engaged only by relatively soft material of the strip 26. Furthermore, the pressure on a blood vessel may be readily adjusted, and when the clamp is at least partially closed, a blood vessel cannot be displaced sideways out of the clamp.

Although a single embodiment of the present invention has been described and illustrated, it will be apparent to those skilled in the art that various modifications may be made without departing from the principles of the invention.

What is claimed is:

1. A surgical clamp comprising a pair of arms, each arm being interconnected at one end to one end of the other arm by a flexible, resilient member normally urging said arms apart while maintaining facing surfaces, said resilient member permitting said arms to be moved toward each other until they are generally parallel, a clamping means of resilient material mounted in said arms, said resilient material being softer than the material of said clamping arms, and releasable ratchet means at the opposite end of one of said arms extending toward and being engageable with holding means on the other of said arms, so that when the arms are moved toward each other, the arms can be held in fixed relative positions, said ratchet means including a ratchet body, a flexible tubing mounted to said ratchet body and a guide member extending outwardly at an angle away from the ratchet body toward the clamping means to guide a blood vessel into the clamping means.

2. A surgical clamp as claimed in claim 1 wherein said arms, said connecting resilient member and said ratchet means are made of a plastic material and in one piece.

3. A surgical clamp as claimed in claim 1 wherein each arm defines a concave surface which serves as a finger hold.

4. A surgical clamp as claimed in claim 1 wherein said ratchet body includes nipple means extending from said ratchet body, said flexible tubing mounted on said nipple means and extending away from said ratchet body.

5. A surgical clamp as claimed in claim 1 wherein said ratchet means is a body with ratchet teeth on one side extending from said arm toward a throughgoing slot with at least one open end defined in said other arm for receiving said ratchet means and engaging a lip formed by said other arm.

6. A surgical clamp comprising a pair of jaws, each jaw being interconnected at one end to one end of the other jaw by a flexible, resilient member normally urging said jaws apart while maintaining facing surfaces and defining a concave outer surface which serves as a finger hold, slot means are defined in the facing surfaces of said jaws, said resilient member permitting said jaws to be moved toward each other until they are generally parallel, bracket means mounted on said jaws, clamping means comprising a vessel clamping strip of resilient material mounted in aid jaws and retained by said bracket means, said vessel clamping strip overlying facing surfaces of the clamping portions of the jaws, said resilient material being softer than the material of said clamping jaws, and releasable ratchet means at the opposite end of one of said jaws extending toward and being engageable with holding means on the other of said jaws so that when the jaws are moved toward each other, the jaws can be held in fixed relative positions, said ratchet means including a ratchet body and flexible tubing mounted to said ratchet body, said ratchet body being provided with nipple means which engages and holds said flexible tubing, said flexible tubing providing positioning means to position said clamp around said blood vessel.

7. A surgical clamp as claimed in claim 6 wherein each jaw is provided with bracket means to hold a vessel clamping strip.

8. A surgical clamp as claimed in claim 6 wherein said vessel clamping strip comprises a flexible strip member, a projection member extending outward from each end portion of said flexible strip member, each said projection member being adapted to be received in slot means formed in each of said jaw members.

9. A surgical clamp comprising a pair of jaws, each jaw being interconnected at one end to one end of the other jaw by a flexible, resilient member normally urging said jaws apart while maintaining facing surfaces, said resilient member permitting said jaws to be moved toward each other until they are generally parallel, retaining means mounted on said jaws, clamping means comprising a vessel clamping strip of resilient material mounted in said jaws and retained by said retaining means, said vessel clamping strip overlying facing surfaces of the clamping portions of the jaws, said resilient material being softer than the material of said clamping jaws, and releasable ratchet means at the opposite end of one of said jaws and extending toward and being engageable with holding means on the other of said jaws so that when the jaws are moved toward each other, the jaws can be held in fixed relative positions, said ratchet means including a ratchet body, an elongated member secured to said body and angularly extending from said body towards said vessel clamping strip to form a guide for a blood vessel into said clamping means and flexible tubing mounted to said ratchet body.

10. A surgical clamp as claimed in claim 9 wherein said vessel clamping strip comprises a flexible strip member, a projection member extending outward from each end portion of said flexible strip member, each said projection member being adapted to be received in slot means formed in each of said jaw members.

* * * * *